US008039819B2

(12) United States Patent
Faure et al.

(10) Patent No.: US 8,039,819 B2
(45) Date of Patent: Oct. 18, 2011

(54) DEVICE AND METHOD FOR CREATING A SPATIAL DOSE DISTRIBUTION IN A MEDIUM VOLUME

(75) Inventors: Jérôme Faure, Cachan (FR); Yannick Glinec, Montrouge (FR); Victor Malka, Paris (FR); Thomas Fuchs, Heidelberg (DE); Hanitra Szymanowski, Heidelberg (DE); Uwe Oelfke, Dossenheim (DE)

(73) Assignees: Ecole Polytechnique (FR); Deutsches Krebsforschungszentrum (DE)

( * ) Notice: Subject to any disclaimer, the term of this patent is extended or adjusted under 35 U.S.C. 154(b) by 749 days.

(21) Appl. No.: 11/996,292

(22) PCT Filed: Jul. 20, 2006

(86) PCT No.: PCT/EP2006/064453
§ 371 (c)(1),
(2), (4) Date: Jul. 9, 2008

(87) PCT Pub. No.: WO2007/010020
PCT Pub. Date: Jan. 25, 2007

(65) Prior Publication Data
US 2008/0298401 A1 Dec. 4, 2008

(30) Foreign Application Priority Data
Jul. 20, 2005 (EP) .................................. 05291552

(51) Int. Cl.
*H01S 3/098* (2006.01)
(52) U.S. Cl. .............. 250/492.1; 250/396 R; 250/503.1; 250/505.1; 250/493.1; 315/501; 315/505; 315/507; 315/111.01; 385/147
(58) Field of Classification Search ........................ None
See application file for complete search history.

(56) References Cited

U.S. PATENT DOCUMENTS

| 2,931,941 A | | 4/1960 | Dewey et al. |
| 5,637,966 A | * | 6/1997 | Umstadter et al. ............ 315/507 |
| 5,789,876 A | | 8/1998 | Umstadter et al. |

(Continued)

FOREIGN PATENT DOCUMENTS
EP        1575059        9/2005
(Continued)

OTHER PUBLICATIONS

Malka et al., "Electron Acceleration by a Wake Field Forced by an Intense Ultrashort Laser Pulse", Science, (2002), pp. 1596-1600.*

(Continued)

*Primary Examiner* — Robert Kim
*Assistant Examiner* — Michael Logie
(74) *Attorney, Agent, or Firm* — Adeli & Tollen LLP

(57) ABSTRACT

A device and a method for creating a spatial dose distribution in a medium volume (22) are described. A laser system produces laser pulses (12) with a pulse length shorter than 200 fs (femtoseconds) and is capable to be focused to peak intensities greater than 10^18 W/cm^2 (watts per centimeter squared). An electron source (18) is capable of releasing a high-energy electron pulse (20), in particular the electrons having an energy greater than 100 MeV, upon irradiation with said laser pulses (12) propagating into the medium volume (22). The light paths (52, 56,58) of at least some of the laser pulses (12) are adjustable in such a way that high-energy electron pulses (20) are emitted from the irradiated at least one electron source on different trajectories (20,28,60,62) through the medium volume (22) thereby depositing their dose in the medium volume (22) according to a provided pattern.

10 Claims, 3 Drawing Sheets

U.S. PATENT DOCUMENTS

Figure 1:
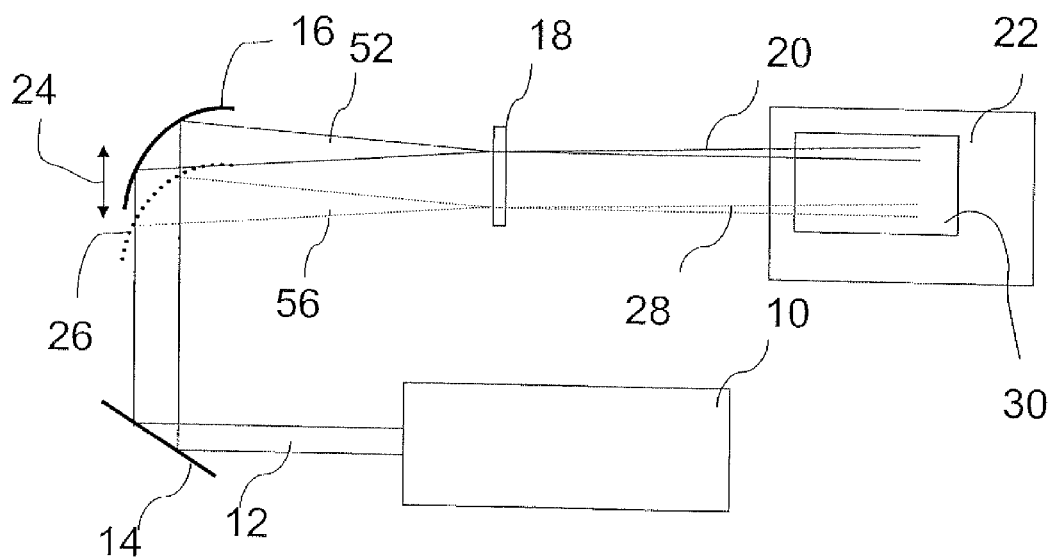

| | | | |
|---|---|---|---|
| 6,333,966 B1 * | 12/2001 | Schoen | 378/119 |
| 7,321,604 B2 * | 1/2008 | Umstadter et al. | 372/2 |
| 7,348,569 B2 * | 3/2008 | Feurer et al. | 250/400 |
| 7,764,373 B2 * | 7/2010 | Fujii et al. | 356/318 |
| 2002/0090194 A1 * | 7/2002 | Tajima | 385/147 |
| 2003/0183774 A1 * | 10/2003 | Tajima | 250/423 P |
| 2004/0018700 A1 * | 1/2004 | Cowan et al. | 438/513 |
| 2004/0195951 A1 * | 10/2004 | Suk et al. | 313/359.1 |
| 2005/0147147 A1 * | 7/2005 | Umstadter et al. | 372/73 |
| 2006/0145088 A1 * | 7/2006 | Ma | 250/396 ML |

FOREIGN PATENT DOCUMENTS

| | | |
|---|---|---|
| EP | 1745821 | 1/2007 |
| EP | 1909907 | 4/2008 |
| WO | WO 2004/057625 | 7/2004 |
| WO | WO 2004/109717 | 12/2004 |
| WO | WO 2006/083300 | 8/2006 |
| WO | WO 2007010020 | 1/2007 |

OTHER PUBLICATIONS

Glinec et al. "Generation of quasi-monoenergeic electron beams using ultrashort and ultraintense laser laser pulses", Laser and particle Beams (2005), 23, 161-166.*

Partial European Search Report and Opinion for EP05291552.7, Jan. 5, 2006 (mailing date), Ecole Polytechnique, et al.

International Search Report for PCT/EP2006/064453, Nov. 22, 2006 (mailing date), Ecole Polytechnique, et al.

International Preliminary Report on Patentability and Written Opinioin for PCT/EP2006/064453, Jan. 22, 2008 (mailing date), Ecole Polytechnique, et al.

Faure, J. et al., "A laser-plasma accelerator producing monoenergetic electron beams," *Nature*, Sep. 30, 2004, pp. 541-544, vol. 431-issue 7008, Nature Publishing Group, UK, ISSN: 0028-0836.

Kainz, K. K. et al., "Dose properties of a laser accelerated electron beam and prospects for clinical application," *Medical Physics AIP for American Assoc. Phys. Med USA*, vol. 31, No. 7, Jul. 2004, pp. 2053-2067, XP002360529 ISSN:0094-2405.

Portions of prosecution history of EP06777860, Sep. 22, 2010 (mailing date), Ecole Polytechnique, et al.

Updated portions of prosecution history of EP05291552, Dec. 3, 2010 (mailing date), Ecole Polytechnique, et al.

* cited by examiner

DEVICE AND METHOD FOR CREATING A SPATIAL DOSE DISTRIBUTION IN A MEDIUM VOLUME

The invention relates generally to a device and a method for creating a spatial dose distribution in a medium volume, with a laser system producing laser pulses with pulse length shorter than 200 fs (femtoseconds) and capable to be focused to peak intensities greater than $10^{18}$ W/cm$^2$ (watts per centimeter squared) and at least one electron source capable of releasing a plurality of high-energy electron pulses upon irradiation with said laser pulses, said high-energy electron pulses propagating into the medium volume.

Accelerated electrons are frequently used in radiotherapy for cancer treatment by exposing the cancer tissue to the particle flux delivering an ionising dose. Common techniques use intensity modulation or fluence attenuation and/or scanning of the electron beam in order to shape the electron flux, and in consequence the dose distribution, to the contour of a medium volume to be treated, see for instance Phys. Med. Biol., vol. 43, 1159-1168 (1998) by Karlsson et al. and Phys. Med. Biol., vol 45, 2293-2311 (2000) by Ma et al. However, the range of application is rather restricted for energies achievable by conventional accelerators since the penetration depth of those electrons is relatively shallow. Feasibility studies and simulations were made for instance in Phys. Med. Biol., vol. 45, 1781-2805 (2000) by DesRosiers et al., in Phys. Med. Biol., vol. 47, 1285-1301 (2002) by Yeboah et al., and Phys. Med. Biol., vol. 47 (2002) 2247-2261 (2002) in order to explore the use and advantages of multi-hundred MeV electron beams in radiotherapy. Those documents are silent about the actual creation of such high-energy electrons and refer only to existing prohibitively large scale installations, such as the Oak Ridge accelerator facility.

Alternatively to conventional accelerators, a method and a device for generating a collimated beam of high-energy particles, such as electrons, using laser-plasma interaction is disclosed for instance in document US 2002/0172317A1 by Maksimchuk et al., in document US 2003/01383774A1 by Tajima, and in document Medical Physics, vol. 31(7), pp 2053-2067 (2004) by Kainz et al. In comparison to conventional accelerators the spectral energy distribution of the electrons is very broad. The maximal achievable energy is not sufficient for novel applications.

A more advanced accelerator is described in document "A laser-plasma accelerator producing monoenergetic beams" in Nature, vol. 431, pp. 541-544 (2004), hereby entirely incorporated by reference into this specification. By focusing an ultra-intense and ultra-short laser pulse onto a material target under certain conditions, an underdense plasma can be produced. It is possible to generate a very strong electrical field, more than a few hundred GV/m (gigavolt per meter), capable to accelerate particles, in particular electrons, from the plasma to high energies and into a collimated and pulsed beam on a very short length scale in comparison to conventional particle accelerators, such as cyclotrons or the like. Basically, in response to the impinging powerful laser pulse, electrons are accelerated to relativistic energies and ejected from the plasma. Among the different laser-driven acceleration mechanisms in the prior art (e.g. the direct laser acceleration, the plasma beat wave acceleration, or the self-modulated laser wakefield acceleration), the non-linear behaviour of the plasma waves in the forced laser wakefield regime drives the generation of highly energetic and low-emittance electron beams. This short pulse electron source has a diameter comparable to the laser beam waist, in particular only several tenth of μm (micrometers).

Although it was assessed that the narrow electron pulses with small divergence and being quasi-monoenergetic, consisting for instance of 170±20 MeV electrons, are well suited for delivering into a medium a deeply penetrating high dose distribution peaked on the propagation axis and featuring a sharp and narrow transverse penumbra, it has turned out that the high energy of the electrons requires an extensive mechanism if scanning a plurality of electron pulses over a medium volume is to be performed in the conventional way by deflecting the electrons.

It is an object of the present invention to provide an alternative device and an alternative method for producing a collimated beam of electrons suitable for cancer treatment, in particular in intensity modulated radiation therapy (IMRT).

The technical problem to solve is to conceive a device and a method for creating a spatial dose distribution in a medium volume using high-energy electrons.

This problem is solved by a device for creating a spatial dose distribution with the limitations according to claim 1 and/or by a method for creating a spatial dose distribution with the limitations according to claim 10. Further improvements and advantageous embodiments and refinements are defined by the limitations set out in the dependent claims.

According to the invention a device for creating a spatial dose distribution in a medium volume (also described as a material volume or an irradiation region) is provided which comprises a laser system producing laser pulses with pulse length shorter than 200 fs (femtoseconds), preferred shorter than 100 fs or even 70 fs, especially shorter than or equal to 50 or even 30 fs, and capable to be focused to peak intensities greater than $10^{18}$ W/cm$^2$, preferred greater than $10^{19}$ or even $10^{20}$ W/cm$^2$ (watts per centimeter squared), at least one electron source, being capable of releasing a plurality of high-energy electron pulses, in particular the electrons having an energy greater than 100 MeV, preferably greater than 150 MeV, upon irradiation with said laser pulses, said high-energy electron pulses propagating into the medium volume, and a control unit, in particular a laser control unit. According to the invention said control unit, in particular said laser control unit, being capable to adjust (also in the sense of to move or to modify or to regulate or to alter or to change) the light paths of at least some of the laser pulses in such a way that high-energy electron pulses are emitted from the at least one irradiated electron source on different trajectories through or into the medium volume thereby depositing their dose in the medium volume according to a provided (e.g. selected or prescribed or specified or the like) pattern.

The general idea of the present invention is to use high-energy electrons generated under well-determined conditions as disclosed in Nature, vol. 431, pp. 541-544 (2004) with an ultra-intense laser in dose distribution delivery into a medium volume, in particular for cancer treatment, preferably in IMRT. Preferably, the laser pulses are focused onto the one electron source or the plurality of electron sources. In particular, the light path extends from the laser system to the at least one electron source. In particular, the electron pulse is collimated featuring a small emittance or divergence, in particular a divergence angle smaller than 20 mrad, preferred 10 mrad, for the full width half maximum of the pulse. The electrons can be quasi-monoenergetic, in particular monoenergetic, with a narrow energy distribution. The material volume can contain biological material or tissue. The dose is defined as absorbed energy per mass and measured in units of Gray (Gy). The pattern can be three-dimensional or two-dimensional or one-dimensional. The pattern can be provided from a radiotherapy treatment planning system. The trajectory of a high-energy electron pulse is the trajectory of the centre of the pulse, e.g. the propagation direction of the central axis of the pulse. The control unit can comprise a storage means in which data is stored comprising the dose pattern and/or data is stored comprising the fluence distribution or fluence pattern of the electron pulses corresponding to, related to or leading to the dose pattern and/or data is stored comprising the light distribution or light pattern, in particular the light path coordinates and/or distribution of number of laser shots and/or distribution of laser intensity and/or distribution of position of the at least one electron source. The device can comprise light guiding elements, for instance mirrors, whose position can be controlled or influenced so that the light path is adjusted or changed. The information about the pattern can be entered into the control unit via a data link (in particular directly) from the radiotherapy planning system, a portable data carrier, or via an interface by a device operator.

Advantageously, using the invention a plurality of electron pulses can deliver a dose distribution in the medium volume so that a high dose is applied to a target volume, e.g. into a cancer tissue or a tumor, and a low dose is applied outside the target volume, e.g. into healthy tissue, in the medium volume. The electrons are suitable for radiotherapy due to their narrow spectral energy distribution. The high-energy electrons can be used to irradiate deep-seated tumors using a scanning system. IMRT applications are feasible.

In a preferred embodiment the laser system of the source according to the invention is a chirped pulse amplification (CPA) facility, in particular a double-CPA laser system, of a self mode-locked Ti:Sapphire laser with output energy greater than 1.6 J (0.6 J on target), output power greater than 20 TW, especially greater than 100 TW, and can have a repetition rate greater than 5 Hz, preferably especially equal to or greater than 10 Hz, the laser being capable of emitting laser pulses shorter than 40 fs, preferably shorter than or equal to 30 fs.

Alternatively or in addition to the feature that the control unit is capable to adjust or change the light paths of the laser pulses, but apart from that with the same features described above, the density of the at least one electron source is adjustable or controlled. By varying the density of the electron source the number of electrons generated upon irradiation with a comparable laser pulse can be changed. Preferably, said adjustment or control is performed by the control unit, in particular the laser control unit. The control unit can comprise a storage means in which data is stored comprising the density pattern.

According to the invention the at least one electron source can be a fluid jet in particular a gas jet. In an advantageous embodiment the gas jet is a supersonic jet, preferably a supersonic Helium gas jet. The gas jet, in particular the supersonic Helium gas jet, can have about 3 mm diameter and/or can provide an initial plasma electron density of the order of $10^{18}$ electrons/$cm^3$, in particular of $7.5 \times 10^8$ electrons/$cm^3$.

In a first preferred embodiment of the device for creating a spatial dose distribution the light path of the laser pulses is relatively movable to the position of the at least one electron source. The electron source can be extended in space, in particular two-dimensional, and the light path can be arranged so that different laser pulses hit the electron source in different positions or at different points. In consequence the generated electron pulses have different trajectories from the electron source to the medium volume. In a second preferred embodiment of the device for creating a spatial dose distribution the light path of the laser pulses and at least one of the at least one electron source are movable in a correlated or co-operative manner. This is a particularly useful arrangement when the electron source is spatially restricted, small or not too extended. In other words, both the light path and the trajectory of the electron pulse can change together in space and, hence, the electrons have a different path into the medium volume.

In a particularly advantageous embodiment of the device for creating a spatial dose distribution, a plurality of light paths extend to a plurality of electron sources. The electron sources are arranged in the three dimensional space surrounding the medium volume, in particular in the vicinity of the medium volume. The embodiment also comprises a switching means for distributing laser pulses onto said light paths. A suitable geometry in this topology enables an irradiation of the medium volume from a plurality of directions.

In a further refinement of the invention the device can comprise generating means creating a magnetic field, for instance permanent magnet structures or electromagnets, downstream from at least one of the at least one electron source and being passed by the short pulses of high-energy electron pulses. On the one hand, the magnetic field can be so strong that the trajectories of the electrons are significantly changed, on the other hand, a weak magnetic field can serve to perform an adjustment or correction operation on the trajectories of the is electrons. The magnetic field can have a focussing effect onto the electron pulses and/or the magnetic field can have a velocity-selecting effect onto the electron pulses. The dose deposition can be advantageously improved by focussing the electron pulse. In addition or alternatively to the focussing the energy range of the electrons can be selected by a velocity filter, e.g. a magnetic field zone and slits.

There is also provided a method for creating a spatial dose distribution in a medium volume. In the method laser pulses with a pulse length shorter than 200 fs (femtoseconds), preferred shorter than 100 fs or even 70 fs, especially shorter than or equal to 50 or even 30 fs, and capable to be focused to peak intensities greater than $10^{18}$ W/$cm^2$, preferred greater than $10^{19}$ or even $10^{20}$ W/$cm^2$ (watts per centimeter squared), are produced. At least one electron source which is capable of releasing a high-energy electron pulse upon irradiation with at least one of said laser pulses is irradiated with at least one of said laser pulses. In particular, the electrons have an energy greater than 100 MeV, preferably greater than 150 MeV. The electron pulses are propagating into said medium volume. In particular, the laser pulses or their propagation direction and/or propagation paths are controlled. The light paths of at least some of the laser pulses are adjusted (also in the sense of moved or modified or regulated or altered or changed) in such a way that high-energy electron pulses are emitted from the at least one irradiated electron source on different trajectories through or into the medium volume thereby depositing their dose in the medium volume according to a provided (e.g. selected or prescribed or specified or the like) pattern.

In a particularly advantageous embodiment of the method according to the invention the medium volume is irradiated with high-energy electron pulses from a plurality of different directions.

In a preferred embodiment of the method according to the invention the at least one laser pulse is propagated to said at least one electron source under vacuum condition. The interaction at the electron source itself takes place under vacuum condition, too. Both measures independently from each other reduce advantageously the risk of degradation of the laser pulses.

The device and the method according to this specification provide high-energy electrons which can broadly and advantageously be used in medical applications, radiological applications, radiobiological applications, radiochemical applications, or applications in physical engineering, or in material engineering, e.g. non-destructive material or mechanical inspection.

Further improvements, refinements and advantageous embodiments, features and characteristics are described below and explained in more detail by referring to the attached drawings. It should be understood that the detailed description and specific examples given, while indicating the preferred embodiment, are intended for purpose of illustration and are not intended to unduly limit the scope of the present invention.

Figure 2:
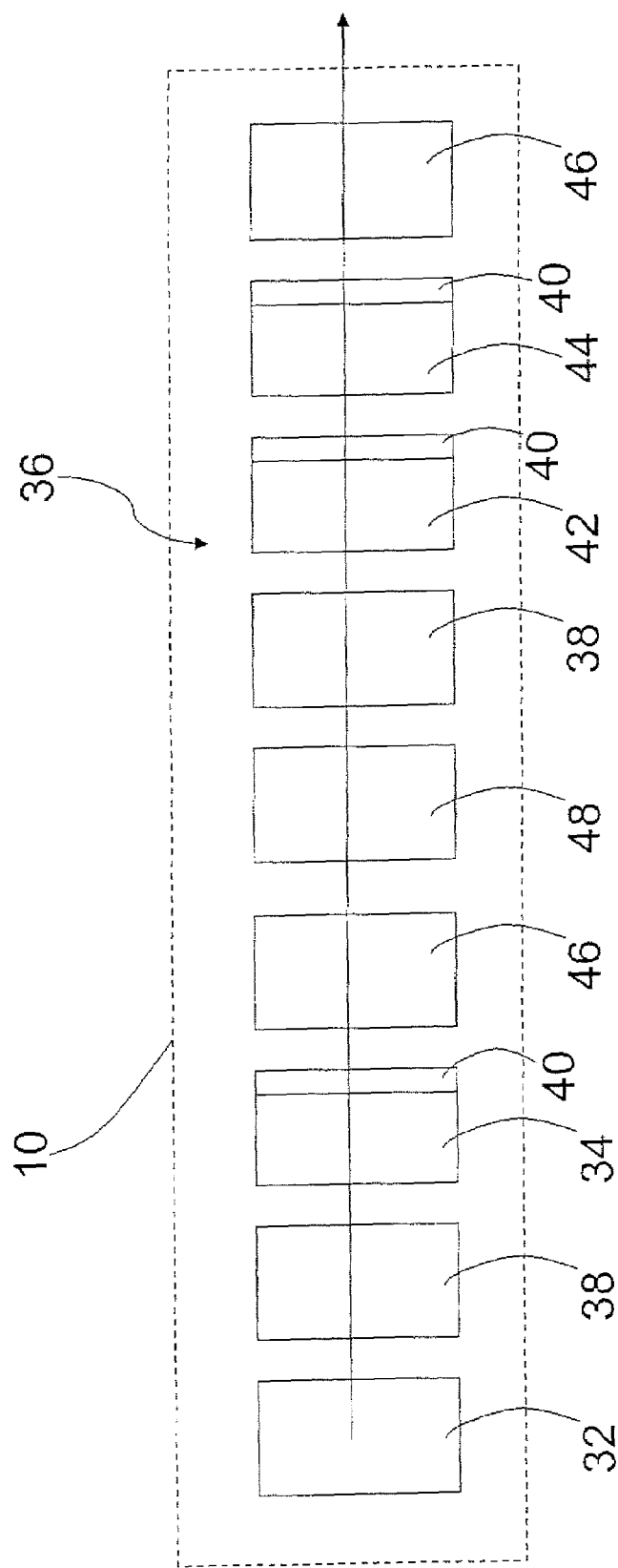
Figure 3:
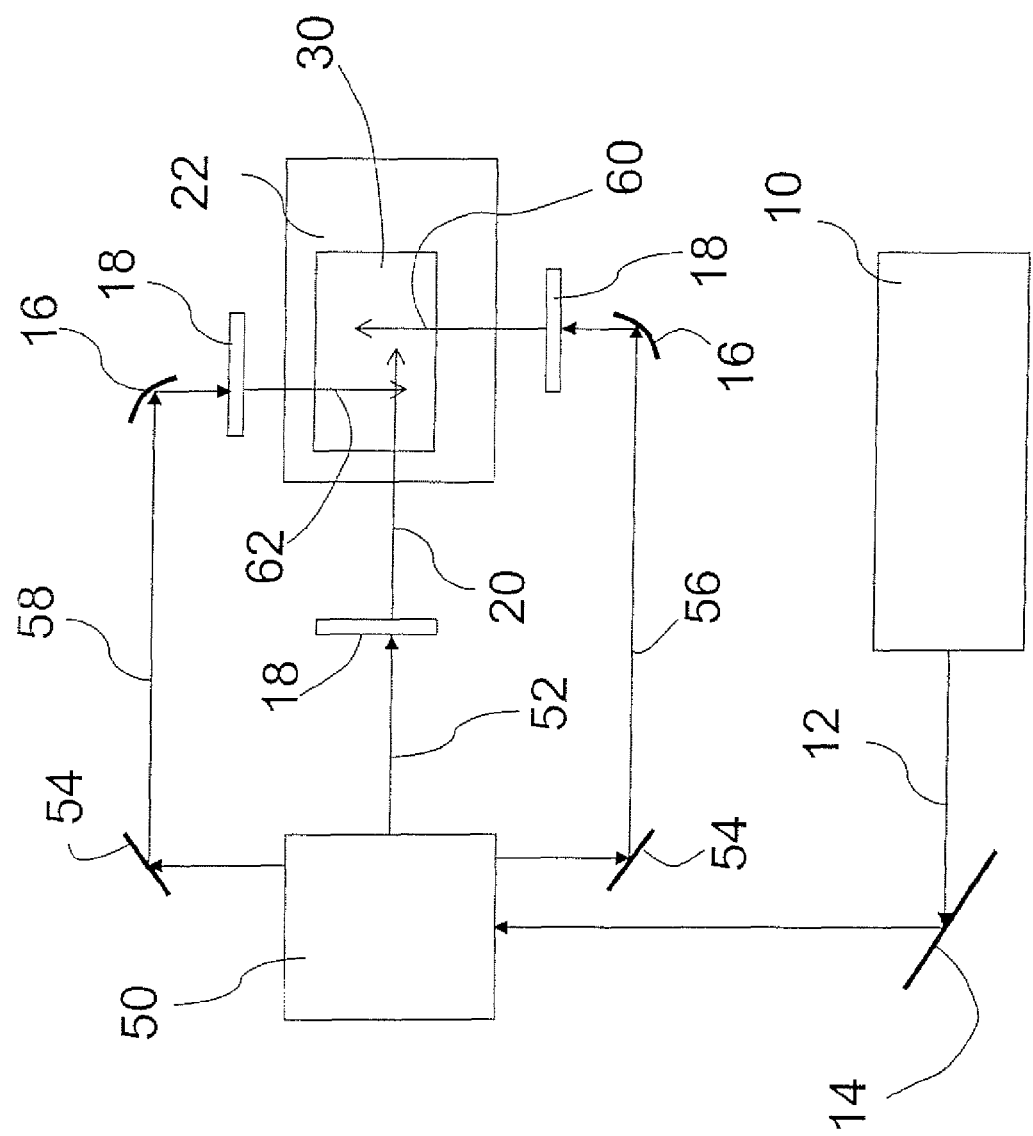

The various features, advantages and possible uses of the present invention will become more apparent in the following description and the attributed drawings, wherein:

FIG. 1 is showing a schematic representation of the topology of a preferred embodiment of the device for creating a spatial dose distribution in a medium volume according to the invention, FIG. 2 is showing a scheme of the preferred embodiment of the chirped pulse amplification (CPA) laser facility used in the device according to the invention, and FIG. 3 is showing a schematic representation of the topology of an advantageous embodiment of the device for creating a spatial dose distribution with a plurality of electron sources.

In FIG. 1 a schematic representation of the topology of a preferred embodiment of the device for creating a spatial dose distribution in a medium volume is shown. A laser system 10 is capable of emitting a train of sub-picosecond ultra-intense laser pulses 12 shorter than 200 fs, in this embodiment 30 fs, which can be focused to peak intensities greater than $10^{18}$ W/cm$^2$, in this embodiment to about $3.2*10^{18}$ W/cm$^2$, corresponding to a normalised vector potential of 1.3 well in the relativistic regime. The laser output consists of laser pulses 12 which have an advantageously steep rising edge (see also below in conjunction with FIG. 2). A laser pulse 12 contains about 1 J energy at 820 nm central wavelength. Delivery optics 14 which may comprise light guiding elements, such as mirrors, divergence or emittance converting elements or the like, schematically represented here in FIG. 1 by a simple mirror, guide the laser pulses 12 to a reaction or interaction volume. The laser pulses are focused with the aid of a focussing mirror 16, preferably an f/18 off-axis parabolic mirror, onto an electron source 18 along a first light path 52. The electron source 18 is a fluid jet, in preferred embodiment a supersonic Helium gas jet with 3 mm diameter. The electron source 18 is preferably positioned in the focus or close to the focus, for instance in the Rayleigh range of the focus, of the laser pulses 12. Upon irradiation an initial electron density in the plasma of $6*10^{18}$ electrons/cm$^3$ is created. The interaction of the laser pulses 12 with the electron source 18 yields a highly collimated (very low emittance) electron pulse 20 emitted essentially perpendicular to the rear surface of the electron source 18. The direction of travel of the electron pulses 20 is determined by the irradiating laser pulses 12.

Downstream from the electron source 18 a medium volume 22 is shown. The medium volume 22 comprises a target volume 30 into which a high dose should be delivered. The electron pulse 20 is smaller than the medium volume 22 and also smaller than the target volume 30. In order to scan a plurality of electron pulses 20 through or over the medium volume 22, more precisely the target volume 30 in the medium volume 22, the electron pulses 20 and the medium volume 22 must be moved relative to each other. In practice, it is not useful or recommended to move the medium volume 22—except for tiny corrections or adjustments—for avoidance of positional errors or uncertainties. However, it might be that the medium volume 22 can substantially be translated in one-dimension. In order to move the electron pulses 20 according to the invention the laser pulses 12 impinging onto the electron source 18 are moved.

In the preferred embodiment shown in FIG. 1 the focussing mirror 16 can be moved, the displacement being indicated by double-arrow 24, without restriction of generality in this example in one dimension. The displacement is executed by the control unit (not graphically shown). When the focussing mirror is in a displaced position 26 the light pulses 12 are focussed onto the electron source 18 along a second light path 56 different or distinct from the first light path 52. The interaction of the laser pulses 12 with the electron source 18 yields a highly collimated (very low emittance) electron pulse 28 emitted on a second trajectory different from the trajectory of the electron pulse 20 but also travelling into the medium volume 22. Displacement of the parabolic mirror 16 in direction of double-arrow 24 allows scanning of the electron pulses through the medium volume 22.

It is clear from these illustrative explanations that, in general, in an advantageous embodiment of the device and method according to the invention the laser pulses 12 can be moved in at least two linear independent directions so that scanning of the electron pulses 20 is achieved over a two-dimensional surface, section or plane, in particular of the target volume 30 in the medium volume 22. In particular, the light paths of the laser pulses 12 can be changed parallel to the direction of the fluid jet, and the fluid jet and the light paths of the laser pulses 12 can be moved in a correlated manner lateral and perpendicular to the direction of the fluid jet.

The entire device can be arranged inside a vacuum chamber. Alternatively, the laser pulses 12 can be conveyed from a laser table to the reaction volume in a vacuum chamber housing the electron source 18. The laser pulses 12 can be guided under vacuum conditions to the volume. In any embodiment the device according to the invention is very compact in comparison to conventional accelerators.

In FIG. 2 a scheme of the preferred embodiment of the laser system used in the device and method according to the invention is shown. The laser system is a so-called double-CPA laser system. It operates in chirped-pulse amplification mode at 820 nm (nanometer) central wavelength. A mode-coupled oscillator 32 comprises a Titanium:Sapphire crystal which is pumped by an Argon-ion laser. The oscillator 32 output consists of femtosecond pulses, in particular essentially 15 fs long, with an energy of 2 nJ with a repetition rate of approximately 88 MHz. The oscillator 32 pulses are stretched by a pair of optical gratings in stretcher 38 (pulse chirping) and an acousto-optical modulator is used afterwards to select individual pulses at a frequency of 10 Hz out of the high-frequency pulse train leaving the oscillator 32 and the stretcher 38. After that pulses essentially 400 ps long and with an energy of about 500 pJ enter an 8-pass pre-amplifier 34. The pre-amplifier 34 is pumped by a frequency-doubled pulsed Nd:YAG laser with 200 mJ energy per pulse at a frequency of 10 Hz. Stretcher 38 and pre-amplifier 34 are optically isolated using an arrangement of a Pockels cell between polarizers. The output of pre-amplifier 34 passes through a spatial filter 40 (afocal ×4) and conveys an energy of 2 mJ per pulse. Now the 10 Hz pulse train is partially or totally recompressed (compressor 46, pulse dechirping) and passes a device 48 for shaping the temporal intensity profile (preferred topology after the pre-amplification stage). It is advantageous to increase the laser contrast, meaning the difference in intensity between the maximum and the leading edge (of the wing) of the pulse, by shaping the temporal intensity profile right after the pre-amplification stage. The device 48 is followed by a second stretcher 38 (pulse chirping) and by a main amplifier 36. The main amplifier 36 comprises a 5-pass first power amplifier 42 pumped by a frequency-doubled pulsed Nd:YAG laser with 1 J energy per pulse at 10 Hz. The pulses amplified to 200 mJ energy pass through a spatial filter 40, preferably a vacuum spatial filter (afocal ×4) and enter a 4-pass second power amplifier 44 of the main amplifier 36. The crystal of the second power amplifier 44 is contained in a cryogenic chamber at 120 K temperature. Several frequency-doubled pulsed Nd:YAG lasers pump this amplification stage: Three lasers at 1.7 J, three lasers at 1.5 J, an one laser at 1.7 J are used. This arrangement results in an output of pulses being 400 ps long and having an energy of 3.5 J. After the second amplification a spatial filter 40, preferably a vacuum spatial filter (afocal ×1) is traversed. The pulses are eventually compressed in a vacuum compressor 46 (pulse dechirping) using a pair of optical gratings reaching pulses being 30 fs to 25 fs long (full width half maximum) and having an energy of 2.5 J. The waist of the focal spot is 18 µm, resulting in vacuum focused intensities of the order of $4\times10^{18}$ W/cm$^2$, which corresponds to a normalised laser vector potential of 1.4, reaching on-target energies of 1.3 J.

In FIG. 3 a schematic representation of the topology of an advantageous embodiment of the device for creating a spatial dose distribution with a plurality of electron sources is shown. Light pulses 12 emitted from laser system 10 are guided by a delivery optics 14, schematically represented by one mirror, to a switching means 50 capable to distribute the laser pulses 12 onto different paths 52,56,58 to a plurality of electron sources 18, in this exemplary embodiment three, surrounding a medium volume 22 comprising a target volume 30. The switching means 50 is regulated by a control unit (not shown). The distribution of laser pulses 12 is arranged according to the provided pattern so that the medium volume 22 can be irradiated out of several different directions. The laser pulses 12 travelling along the first light path 52 are focussed onto an electron source 18 thereby generating a high-energy electron pulse 20 propagating into the medium volume 22 on a first trajectory. Other laser pulses 12 are diverted onto a second light path 56. Light guiding elements 54 are used to transport the laser pulses 12 to a focussing mirror 16, preferably a parabolic mirror, projecting the laser pulses 12 onto an electron source 18 generating a high-energy electron pulse 60 propagating into the medium volume 22 on a second trajectory. Again other laser pulses 12 are sent onto a third light path 58. Light guiding elements 54 are used to transport the laser pulses 12 to a focussing mirror 16, preferably a parabolic mirror, projecting the laser pulses 12 onto an electron source 18 generating a high-energy electron pulse 62 propagating into the medium volume 22 on a third trajectory.

In addition to the irradiation out of three different directions as explained in conjunction with FIG. 1 each light path of the different light path 52,56,58 can also be adjusted in order to change the trajectory of the electron pulses 20,60,62 into the medium volume (not explicitly shown in FIG. 3). In other words, each plurality of electron pulses 20,60,62 emitted from each of the electron sources 18 can be scanned through the medium volume. The trajectories of the electron pulses from different direction can partially overlap or intersect.

REFERENCE NUMERAL LIST

10 laser system
12 sub-picosecond laser pulse
14 delivery optics
16 focusing mirror
18 electron source
20 electron pulse
22 medium volume
24 displacement of focussing mirror
26 position of displaced focussing mirror
28 electron pulse on different trajectory
30 target volume
32 oscillator
34 pre-amplifier
36 main amplifier
38 stretcher
40 spatial filter
42 first power amplifier
44 second power amplifier
46 compressor
48 device for shaping the temporal intensity profile
50 switching means
52 first light path
54 light guiding element
56 second light path
58 third light path
60 electron pulse on second trajectory
62 electron pulse on third trajectory

The invention claimed is:

1. A device for creating a spatial dose distribution in a medium volume, the device comprising:
    a laser system producing laser pulses with a pulse length shorter than 200 fs and capable to be focused to peak intensities greater than $10^{18}$ W/cm$^2$;
    at least one electron source for releasing a plurality of high-energy quasi-monoenergetic electron pulses upon irradiation with said laser pulses, said high-energy quasi-monoenergetic electron pulses propagating into the medium volume, said high-energy quasi-monoenergetic electron pulses comprising electrons having an energy greater than 100 MeV;
    a control unit comprising data storage that stores a provided pattern, said provided pattern comprising at least one of (i) a dose pattern, (ii) an electron fluence pattern and (iii) a light pattern, said control unit for adjusting light paths of at least some of the laser pulses in such a way that high-energy quasi-monoenergetic electron pulses are emitted from the irradiated at least one electron source on different trajectories through the medium volume thereby depositing their dose in the medium volume according to said provided pattern.

2. The device for creating a spatial dose distribution in a medium volume according to claim 1, wherein the laser system is a chirped pulse amplification facility of a self mode-locked Ti:Sapphire laser, with an output energy greater than 0.6 J and an output power greater than 20 TW, for emitting laser pulses shorter than 40 fs.

3. The device for creating a spatial dose distribution in a medium volume according to claim 1, wherein the density of the at least one electron source is adjustable.

4. The device for creating a spatial dose distribution in a medium volume according to claim 1, wherein the at least one electron source is a fluid jet.

5. The device for creating a spatial dose distribution in a medium volume according to claim 4, wherein the fluid jet is a supersonic Helium gas jet for delivering an initial plasma electron density on the order of $10^{18}$ electrons/cm$^3$.

6. The device for creating a spatial dose distribution in a medium volume according to claim 1, wherein a light path of the laser pulses is movable relative to a position of the at least one electron source or the light path of the laser pulses and at least one of the at least one electron source are movable in a correlated manner.

7. The device for creating a spatial dose distribution in a medium volume according to claim 1 further comprising a plurality of light paths to a plurality of electron sources and a switch for distributing laser pulses onto said plurality of light paths.

8. The device for creating a spatial dose distribution in a medium volume according to claim 1 further comprising a magnetic field generator, downstream from at least one of the at least one electron source and being passed by the high-energy quasi- monoenergetic electron pulses, for having at least one of a focusing effect and a velocity selecting effect on said high-energy quasi-monoenergetic electron pulses.

9. A method for creating a spatial dose distribution in a medium volume, the method comprising:

producing laser pulses with a pulse length shorter than 200 fs and comprising peak intensities greater than $10^{18}$ W/cm$^2$;

irradiating, with said laser pulses, at least one electron source capable of releasing a plurality of high-energy quasi-monoenergetic electron pulses, comprising electrons having an energy greater than 100 MeV, said high-energy quasi-monoenergetic electron pulses propagating into the medium volume;

storing a provided pattern, said provided pattern comprising at least one of (i) a dose pattern, (ii) an electron fluence pattern and (iii) a light pattern;

adjusting light paths of at least some of the laser pulses in such a way that high-energy quasi-monoenergetic electron pulses are emitted from the at least one irradiated electron source on different trajectories through the medium volume thereby depositing their dose in the medium volume according to the provided pattern.

10. The method for creating a spatial dose distribution in a medium volume according to claim 9 further comprising irradiating the medium volume with high-energy quasi-monoenergetic electron pulses from a plurality of different directions.

* * * * *